(12) United States Patent
Holmes

(10) Patent No.: US 6,559,175 B1
(45) Date of Patent: May 6, 2003

(54) METHOD OF INSECT CONTROL

(75) Inventor: Keith A. Holmes, Cary, NC (US)

(73) Assignee: Bayer CropScience Inc., Research Triangle Park, NC (US)

(*) Notice: Subject to any disclaimer, the term of this patent is extended or adjusted under 35 U.S.C. 154(b) by 0 days.

(21) Appl. No.: 09/396,331

(22) Filed: Sep. 15, 1999

Related U.S. Application Data

(60) Provisional application No. 60/100,806, filed on Sep. 18, 1998.

(51) Int. Cl.[7] .......................... A01N 43/56; A01N 53/08
(52) U.S. Cl. ..................... 514/407; 514/404; 514/521; 514/531; 504/100
(58) Field of Search ................................ 514/404, 521, 514/407, 531; 504/100

(56) References Cited

U.S. PATENT DOCUMENTS 5,516,787 A    5/1996    Takada ................. 514/407

FOREIGN PATENT DOCUMENTS

| WO | WO 93/06089 | 4/1993 |
|----|-------------|--------|
| WO | WO 95/22902 | 8/1995 |

OTHER PUBLICATIONS

Tomlin, The Pesticide Manual Incorporating The Agrochemicals Handbook, Tenth Edition, (1995), pp. 254 and 255.*

C.D.S. Tomlin (ED.), "The Pesticide Manual," (1997) British Crop Protection Council, Farnham XP002103044.

* cited by examiner

Primary Examiner—John Pak
(74) Attorney, Agent, or Firm—Jenkins & Wilson, P.A.

(57) ABSTRACT

A method of protecting a corn plant from destructive insects which comprises applying to the seed from which it grows or the soil from which the seed grows a composition comprising an insecticidal 1-arylpyrazole and an insect repellent. A composition comprising the insecticidal 1-arylpyrazole and the repellent.

2 Claims, No Drawings

METHOD OF INSECT CONTROL

This application claims the benefit of U.S. Provisional Application No. 60/100,806, filed on Sep. 18, 1998.

The present invention relates to a new method of controlling destructive insects, a new composition and a product which comprises the composition.

It is known that 5-amino-3-cyano-1-(2,6-dichloro-4-trifluoromethylphenyl)-4-trifluoromethylsulfinylpyrazole (fipronil) may be applied to corn seed at the time of planting to protect the said corn seed and the plants which emerge from the seed from inter alia, rootworms, e.g., *Diabrotica undecipuntata howardi* and corn borers, e.g., *Ostrinia nubilalis*. In some cases, however, fipronil provides less than optimum activity against soil born pests, particularly against rootworms generally from the time of planting to the V6 growth stage of the corn plant It is also known to apply insecticidally effective amounts of pyrethroid insecticides at the time of planting to control certain pests, inter alia, rootworms, e.g., *Diabrotica undecipuntata howardi*.

An object of the present invention is to provide an improved method of control of insects, particularly insects destructive to corn.

Another object of the present invention is to provide a long-lasting control of insects destructive to corn.

Another object of the present invention is to provide an improved method of using an insecticidal 1-arylpyrazole.

Another object of the present invention is to provide an improved method of using a pyrethroid insecticide.

These and other objects are met in whole or in part by the present invention.

The present invention provides a method of protecting a corn plant from destructive insects which method comprises applying to the seed from which it grows or the soil from which the seed grows a composition comprising an insecticidal 1-arylpyrazole and an insect repellent, which 1-arylpyrazole is a compound of formula (I):

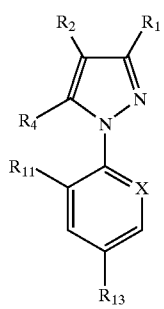

(I)

wherein:
R$_1$ is CN or methyl;
R$_2$ is S(O)$_n$R$_3$;
R$_3$ is alkyl or haloalkyl;
R$_4$ is selected from the group comprising a hydrogen atom, a halogen atom, and a radical which may be —NR$_5$R$_6$, C(O)OR$_7$, —S(O)$_m$R$_7$, alkyl, haloalkyl, —OR$_8$, or —N=C(R$_9$)(R$_{10}$); R$_4$ is preferably a amino group, which is unsubstituted or which bears one or two substituents from the group consisting of alkyl, haloalkyl, acyl and alkoxycarbonyl;
R$_5$ and R$_6$ are independently selected from a hydrogen atom, alkyl, haloalkyl, —C(O)alkyl, —S(O)$_r$CF$_3$; or R$_5$ and R$_6$ form together a divalent radical which may be interrupted by one or more heteroatoms;

R$_7$ is selected from alkyl or haloalkyl;
R$_8$ is selected from alkyl, haloalkyl or the hydrogen atom;
R$_9$ is selected from the hydrogen atom and alkyl;
R$_{10}$ selected from phenyl or heteroaryl that is optionally substituted by one or more hydroxy, a halogen atom, —O-alkyl, —S-alkyl, cyano, or alkyl or combinations thereof;
X is selected from the Nitrogen atom and the radical C—R$_{12}$;
R$_{11}$ and R$_{12}$ are independently selected from a halogen atom or the hydrogen atom;
R$_{13}$ is selected from a halogen atom, haloalkyl, haloalkoxy, —S(O)$_q$CF$_3$, —SF$_5$, preferably from a halogen atom, haloalkyl, haloalkoxy, —SF$_5$;
m,n,q,r are independently selected from 0,1, and 2;
provided that when R$_1$ is methyl, R$_3$ is haloalkyl, R$_4$ is NH$_2$, R$_{11}$ is Cl, R$_{13}$ is CF$_3$, and X is N.

The alkyl and alkoxy groups of the formula (I) are preferably lower alkyl and alkoxy groups, that is, radicals having one to four carbon atoms. The haloalkyl and haloalkoxy groups likewise preferably have one to four carbon atoms. The haloalkyl and haloalkoxy groups can bear one or more halogen atoms; preferred groups of this type include —CF$_3$ and —OCF$_3$.

The preparation of compounds of formula (I) can be effected according to any process described in International Patent Publications No. WO 87/03781, WO 93/06089 and WO 94/21606, as well as in European Patent Publication numbers 0295117, 0403300, 0385809, and 0679650, German Patent Publication 19511269 and U.S. Pat. Nos. 5,232,940 and 5,236,938.

Preferably the compound of formula (I) has one or more of the following features:
R$_1$ is CN;
R$_4$ is —NR$_5$R$_6$;
R$_5$ and R$_6$ are independently selected from the hydrogen atom, alkyl, haloalkyl, —C(O)alkyl, C(O)OR$_7$;
X is C—R$_{12}$; or
R$_{13}$ is selected from a halogen atom, haloalkyl, haloalkoxy, or —SF$_5$.

Most preferably the compound of formula (I) is 5-amino-3-cyano-1-(2,6-dichloro-4-trifluoromethyl)phenyl-4-trifluoromethylsulfinylpyrazole (or fipronil) or 5-amino-3-cyano-1-(2,6-dichloro-4-trifluoromethylphenyl)-4-ethylsulfinylpyrazole hereinafter known as Compound B.

In a preferred embodiment, the repellent is applied in a substantially non lethal amount. By the term "substantially non-lethal" is meant an amount, which when delivered to the soil kills less than 10% of the pests so-controlled by the method of the invention. Preferably the repellant kills less than 5% of the pests.

The repellent may be a known insect repellent. Preferably the insect repellent is a pyrethroid insecticide. Preferably, the repellent is a pyrethroid insecticide that is selected from the grop consisting of tefluthrin, permethrin, fenvalerate, esfenvalerate, cypermethrin, cyhalothrin, lambda-cyhalothrin, bifenthrin and deltamethrin Generally the pests controlled by the method include Agrotis spp., e.g. black cutworm; rootworms, including Diabrotica spp. e.g. *Diabrotica undecipuntata howardi* or *Diabrotica virgifera;* or corn seed maggot, e.g. *Hylemyia platura, Chortophila platura, Chortophila cilicrura, Hylemya cilicrura, Phorbia platura, Hylemya platura, Chortophila funesta, Chortophila fusciceps, Crinura cilicrura, Crinura platura, Crinura fusciceps, Crinura funesta, Delia* cilicrura, Delia funesta, Delia fusciceps, Hylemya funesta, Hylemya fusciceps, Phorbia cilicrura, Phorbia funesta, Phorbia fusciceps, Hylemya cana, Delia cana, Hylemyia cana, or Delia platura Generally, the weight to weight ratio of the insecticidal 1-arylpyrazole to the repellent is from 2:1 to 200:1, preferably from 5:1 to 75:1, most preferably from 8:1 to 50:1.

The composition is generally applied as a liquid composition to the soil or as a seed treatment to the seed from which the corn plant grows.

In a highly preferred embodiment, the liquid composition may be directed into the soil mixing zone below the level of the top of the furrow in which the corn seed may be planted. In this way, the composition may be incorporated in the soil below the level of the soil, on the seed and above the seed as the furrow is closed. The application spray can be a stream of liquid or a conical spray.

Generally the volume of liquid to be used per unit land area is from 0.1 to 50 gallons per acre (0.9 to 470 L/ha), preferably from 0.2 to 10 gal/A (1.9–90 L/ha), more preferably from 0.5 to 5 gal/A (4.7–47 L/ha), most preferably from 1 to 3 gal/A (9.4–28 L/ha).

When the repellent is a pyrethroid insecticide, it is preferably used at about 1% to 90% of the labeled use rate of the repellent, preferably from 5% to 50%. The following table provides a general guidance to preferred rates to be used in the method of the present invention.

| Repellent | Current Field Use Rate in Corn (lb. ai/acre) | Use rate according to the present invention (lb. ai/acre) |
| --- | --- | --- |
| tefluthrin | 0.075–0.15 | 0.001–0.02 |
| esfenvalerate | 0.03–0.05 | 0.001–0.02 |
| lambda-cyhalothrin | 0.015–0.030 | 0.001–0.01 |
| permethrin | 0.1–0.2 | 0.01–0.02 |

The abbreviation "ai" means active ingredient.

The rate of use of the 1-arylpyrazole is generally from 0.01 lb. per acre (11 g per hectare) to about 2.2 lb./acre (1000 g/Ha), preferably from preferably from 20 to 200 g/Ha.

In a highly preferred embodiment of the invention, the composition is applied when the soil temperature is from 4° C. to 25° C., preferably from 10° C. to 20° C. In this way there is a better insecticidal effect on the above insect species than with the 1-arylpyrazole insecticide alone.

The present invention also provides an agriculturally acceptable composition for protecting corn plants from destructive insects which comprises an insecticidal 1-arylpyrazole as defined above and a repellent, preferably a substantially non-lethal amount of an insect repellent as defined above. The composition may be a liquid composition or a granular composition, preferably a liquid composition in use. Liquid compositions include those known to the skilled addressee and emulsifiable concentrates, suspension concentrates or aqueous emulsions are generally preferred.

The present invention also provides a product comprising an insecticidal 1-arylpyrazole as defined above and a repellent for simultaneous, separate or sequential use in the control of destructive insects of corn in or on the soil from which the corn grows. Preferably the product may be a premixed product which comprises both the 1-arylpyrazole and the repellent.

The following non-limiting example demonstrate the invention:

EXAMPLE 1

Corn seed is planted in a field where the average temperature of the soil is about 20° C. As the corn seed is planted, fipronil (as the commercial product REGENT® 80WG) and lambda-cyhalothrin (as the commercial product WARRIOR®) are applied simultaneously on the seed as a liquid composition in water at rates of 0.13 lbs/acre (0.15 kg/Ha) and 0.01 lbs/acre (0.011 kg/Ha) respectively. One part of the field is treated with REGENT® 80WG at 0.13 lbs/acre alone. After 4 weeks, several plants are removed to determine the damage to the roots and stalks. The treatment with fipronil and lambda-cyhalothrin provides a lower numerical Iowa Root rating than the treatment with REGENT® alone. There is less damage from black cutworm in the fipronil+lambda-cyhalothrin treatment than in the fipronil treatment.

What is claimed is:

1. A method of protecting a corn plant from destructive insects, the method comprising applying to one of the seed from which the corn plant grows and the soil from which the seed grows an enhanced insecticidally effective amount of a composition comprising an insecticidal 5-amino-3-cyano-1-(2,6-dichloro-4-trifluoromethylphenyl)-4-trifluoromethylsulfinylpyrazole and lambda-cyhalothrin, wherein the insecticidal 5-amino-3-cyano-1-(2,6-dichloro-4-trifluoromethylphenyl)-4-trifluoromethylsulfinylpyrazole and the lambda-cyhalothrin are present in the composition in a weight ratio of from 8:1 to 50:1 (5-amino-3-cyano-1-(2,6-dichloro-4-trifluoromethylphenyl)-4-trifluoromethylsulfinylpyrazole:lambda-cyhalothrin) and wherein the lambda-cyhalothrin is present in the composition in a substantially non-lethal, repellent amount.

2. A composition comprising the 1-arylpyrazole insecticidal compound 5-amino-3-cyano-1-(2,6-dichloro-4-trifluoromethylphenyl)-4-trifluoromethylsulfinylpyrazole and the insect repellent lambda-cyhalothrin in a weight ratio of from 8:1 to 50:1 (5-amino-3-cyano-1-(2,6-dichloro-4-trifluoromethylphenyl)-4-trifluoromethylsulfinylpyrazole:lambda-cyhalothrin), wherein the insect repellent is present in the composition in a substantially non-lethal, repellent amount, and wherein the composition is adapted for one of simultaneous, separate and sequential use in the control of destructive insects of corn on the soil from which the corn grows.

* * * * *